United States Patent
Okuno et al.

(10) Patent No.: US 6,963,020 B1
(45) Date of Patent: Nov. 8, 2005

(54) DNA POLYMORPHISM-BASED METHODS FOR IDENTIFYING FIELD RESISTANCE OF RICE TO RICE BLAST

(75) Inventors: Kazutoshi Okuno, Ibaraki (JP); Shuichi Fukuoka, Ibaraki (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 0 days.

(21) Appl. No.: 09/560,780

(22) Filed: Apr. 28, 2000

Related U.S. Application Data (60) Provisional application No. 60/131,726, filed on Apr. 30, 1999.

(51) Int. Cl.$^7$ .............................................. A01H 1/04
(52) U.S. Cl. .................................................... 800/267
(58) Field of Search ............................. 800/320.2, 267, 800/265; 438/6, 912

(56) References Cited

OTHER PUBLICATIONS

Fukuoka et al, 1996, International Rice Research Notes 21:50-51.*

Rice Genome Research Program, ftp://rgp.dna.affrc.go.jp/pub/japonicarice/tableall.txt, Sep. 1996.*

Minobe, 2002, GenBank Accession No. D13595.*

\* cited by examiner

*Primary Examiner*—Anne Kubelik
(74) *Attorney, Agent, or Firm*—Townsend and Townsend and Crew LLP (57) ABSTRACT

A method for identifying resistance of a rice plant to rice blast is provided. More particularly, a method for identifying resistance of a rice plant to rice blast by testing a genotype of the rice genome using a DNA marker (G271), which is closely linked to a gene controlling the field resistance to rice blast, is disclosed. The disclosed invention allows for evaluation of the field resistance of a rice plant to rice blast using a DNA marker, thereby allowing for a resistant variety to be conveniently and accurately selected. The disclosed invention contributes to reducing the time and labor that have conventionally been required for cross breeding, and is useful in developing novel rice varieties having a high degree of field resistance to rice blast.

3 Claims, 4 Drawing Sheets

FIG. 1

Chromosomal locations related to field resistance to rice blast, derived from Owarihatamochi

FIG. 4

DNA POLYMORPHISM-BASED METHODS FOR IDENTIFYING FIELD RESISTANCE OF RICE TO RICE BLAST

The present application claims benefit of priority to U.S. Provisional Patent Application No. 60/131,726, filed on Apr. 30, 1999.

BACKGROUND OF THE INVENTION

1. Field of the Invention

The present invention is in the field of plant genetics, and relates to a method for identifying resistance of a rice plant to rice blast. In particular, the present invention relates to a method for identifying field resistance of a rice plant to rice blast by determining a genotype of the genome of a rice plant using a DNA marker which is closely linked to a gene controlling the field resistance to rice blast.

2. Description of the Related Art

Usually, when a plant is infected with a pathogen such as a virus, the plant is inhibited from growing, resulting in eventual death. On the other hand, it has been known that certain plants exhibit resistance to a pathogen. It is believed that such plants have a pathogen resistance gene. Several such resistance genes have been confirmed to exist. However, the ability of a pathogen resistance gene in a plant is generally limited to the particular combination of the plant and the specific pathogen, and a gene expressing resistance to one pathogen may not express a trait of resisting any pathogen.

In the field of breeding and improving of plants, a plant having a pathogen resistance gene or an insect resistance gene has been crossed with another plant which does not have such a pathogen or insect resistance gene but has another desirable trait so as to generate a number of improved varieties into which a genetic trait of disease resistance has been introduced. In view of preventing an ecological pollution and ensuring safety for human bodies, it is believed that the generation of such resistant varieties through crossing will become more and more important in the future as a biological epidemic prevention method which utilizes the organism's innate function and does not require agrochemicals.

Rice blast is a plant disease caused by infection with *Pyricularia oryzae*, and is the most prominent disease for rice. Once a rice plant is infected with this fungus, the disease will generally prevail across the farm to completely destroy all the rice plants in the farm. Thus, rice blast is a serious problem for rice breeders. One way to address this problem is to create a variety resistant to rice blast by conferring the resistance to the rice through cross breeding.

The rice blast resistance gene of a rice plant was first found in Japan (Sasaki, R. Jpn. J. Genetics 1:81–85 (1922)). Thereafter, many genes have been confirmed to be related to the rice blast resistance. By crossing a variety having a rice blast resistance gene (i.e., a rice blast resistant variety) with a variety lacking a rice blast resistance gene (i.e., a rice blast non-resistant variety), it is possible to introduce a new trait of rice blast resistance to a variety which is not resistant to rice blast but has other desirable traits (e.g., early maturity, tolerance to cold injuries, good grain and eating qualities).

In conventional breeding, a field testing method has been employed for testing whether a resistance gene of one variety has been introduced to hybrid progeny lines crossed with another variety. According to this method, an individual to be tested is inoculated with *Pyricularia* oryzas, and the rice blast resistance thereof is identified based on the degree of susceptibility or resistance. However, such a testing method requires: breeding an extremely large number of individuals to be tested: inoculating the individuals with the fungus; breeding the inoculated individuals: and evaluating the degree of susceptibility or resistance to rice blast for each of the individuals to be tested. The series of steps requires substantial labor and time on the order of several months, and is not suitable for quick and efficient development of resistant varieties. Moreover, such a testing method needs to be carried out within a special facility in order to avoid propagation of rice blast to other neighboring farms.

In recent years, various molecular biological techniques have been developed, allowing for organisms, tissues or cells to be tested for the presence of a specific gene for determining the genotype thereof. Thus, when the relationship between a gene and the corresponding trait, i.e., phenotype is specified, the phenotype can be indirectly determined by confirming the presence of the gene.

Exemplary techniques for use in such a genotype analysis include a restriction fragment length polymorphism (RFLP) analysis and a random amplified polymorphic DNAs (RAPD) analysis. The RFLF analysis is based on the difference in the number and length (polymorphism) of the restriction fragments which are obtained by processing a genomic DNA with a restriction enzyme which only acts upon a particular base sequence site. Specifically, when a genomic DNA, which is the principal element of the gene, is digested with a restriction enzyme, many DNA fragments of various lengths are obtained. Different individuals or lines often have very similar numbers and lengths of restriction fragments. Typically, however, various mutations exist in the DNA for each individual, whereby slight differences may be observed in the number and length of the restriction fragments. Such differences are called the "restriction fragment length polymorphism". By comparing the differences, the genotype can be determined. The analysis based on the polymorphism requires a useful DNA marker which is closely linked to a gene locus responsible for a genotype of interest. Therefore, it is necessary to identify such a useful DNA marker in order to improve the reliability of the results of the genotype analysis.

The resistance of a rice plant to rice blast is generally classified into two categories: a true resistance; and a field resistance. The true resistance is controlled by a single gene, which exhibits resistance to rice blast on its own. However, as the blast fungus survives, it may mutate and acquire infectivity to a rice plant which used to exhibit a resistance thereto. Therefore, the true resistance may be suddenly lost. In fact, a case has been known where a resistant rice variety cultivated in a farm was infected with rice blast only after 2 years from the time when the farm started growing the variety. In contrast, a field resistance is controlled by a plurality of, probably several, genes. Thus, even when a part of the resistance controlled by one of the genes is lost, for example, the rice variety can be prevented from being seriously damaged by rice blast by virtue of the remaining resistance controlled by the other genes.

As described above, since the true resistance is controlled by a single gene, the heredity thereof is simple and easy to study. A recent report shows that Pi-b, a resistance gene belonging to the true resistance category, has been isolated (Japanese Laid-Open Publication No. 7-163371). While the field resistance is practically highly valuable, it is relatively more difficult to study than the true resistance because the heredity thereof is complicated and the determination of the degree of resistance is likely to be influenced by environmental conditions. Therefore, the field resistance has not been studied as much as the true resistance.

It has been reported that a number of different gene loci related to the field resistance to rice blast were identified by means of the polymorphic analysis using a conventional gene marker (Goto, I., Ann. Phytophatol. Coc. Jpn. 36:304–312 (1970); Higashi, T. and Saito, S. Japan J. Breed. 35:438–448 (1985); Shinoda, H. et al., Bull. Chugoku Nat. Agric. Exp. Static. A20:1–25 (1971)). However, to the knowledge of the present inventors, no report has shown, that a useful DNA marker has been identified which is closely linked to the gene controlling the field resistance.

Thus, there has been a demand for specifying the gene locus which is related to the field resistance to rice blast so as to identify a DNA marker which is closely linked to the gene controlling the resistance. There has also been a demand for developing a method for conveniently and accurately identifying the genotype for the field resistance using such a DNA marker. Such a method would also be useful for efficiently breeding a resistant variety.

SUMMARY OF THE INVENTION

The present invention is intended to address such demands existing in the art. One aspect of the present invention relates to a method for identifying field resistance of a rice plant to rice blast, including the steps of: extracting a genomic DNA from the rice; and using a DNA marker which is closely linked to a field resistance gene pi21(t) to analyze polymorphism at a site in the genomic DNA corresponding to the DNA marker, thereby determining the presence or absence of the gene.

Another aspect of the present invention relates to a method for breeding a rice variety having field resistance to rice blast, including the steps of: crossing a first rice variety having field resistance to rice blast with a second rice variety lacking the field resistance to rice blast so as to obtain first generation rice varieties; extracting a genomic DNA from each of the first generation rice varieties or progenies thereof; using a DNA marker which is closely linked to a field resistance gene pi21(t) to analyze polymorphism at a site in the genomic DNA corresponding to the DNA marker, thereby determining the presence or absence of the gene; and selecting an individual in which the gene is shown to be present from the first generation rice varieties or the progenies thereof.

The DNA marker may be G271. The polymorphism analysis may be performed by a technique selected from the group consisting of RFLP, RAPD, CAPS, SSR and AFLP.

Thus, the invention disclosed herein makes possible the advantage of allowing for evaluation of the field resistance of a rice plant to rice blast using a DNA marker, thereby allowing for a resistant variety to be conveniently and accurately selected indoor. The present invention contributes to reducing the labor and growth period which have conventionally been required for cross breeding, and is useful in developing a novel rice variety having a high degree of field resistance to rice blast.

This and other advantages of the present invention will become apparent to those skilled in the art upon reading and understanding the following detailed description with reference to the accompanying figures.

DESCRIPTION OF THE SPECIFIC EMBODIMENTS

The present invention will be described by way of illustrative examples with reference to the drawings.

(RFLP Analysis)

RAPD analysis is a preferable technique used in the present invention for detecting polymorphism and thereby determining the genotype. The term "restriction fragment length polymorphism (RFLP)" as used herein refers to polymorphism of DNA fragments obtained by processing a DNA with a restriction enzyme. RFLP occurs due to a difference in the genotype among different varieties/lines. Like the phenotype, RFLP can be used to create a gene map. The term "DNA marker" as used herein refers to any DNA fragment capable of detecting the polymorphism. The principle for creation of a gene map through a linkage analysis is the same as that using a conventional marker gene.

Traits expressed by genes which are adjacent to each other on a chromosome are likely to be inherited together to a descendent. This is caused by linkage between the genes. The linkage frequency of genes (i.e., the genetic distance between genes) can be deduced based on the frequency of chromosomal recombinations which occur in reduction divisions.

In the present specification, the genetic distance is represented in centimorgan (cM), wherein one (1) cM is defined as a distance between loci of two markers which have one recombination for 100 reduction divisions. Centimorgan represents a biological distance between two loci, and may not always coincide with the physical distance therebetween.

When performing a linkage analysis, a hybrid population between varieties or lines which are genetically fixed is typically used. Individuals in the hybrid population are analyzed using DNA markers which exhibit polymorphism between the parents, and the obtained data is used to calculate genetic distances between sets of markers. A linkage map can be created by aligning the markers based on the obtained genetic distances.

A typical procedure for a RFLP analysis will' be described below.

An individual used for the RFLP analysis, e.g., a hybrid rice, is cultivated by an ordinary method, and a tissue for extracting the genomic DNAs is collected from each individual. Any of various party of the plant (e.g., a leaf, a flower, a stalk, a root, a shoot, an embryo, etc.) may be used as the tissue for the DNA extraction.

Then, the whole DNA is extracted from the collected tissues. While any method known to those skilled in the art may be used, a CTAB method (Murray M. G. and Thompson W. F., Nucleic Acid Res., 8:4321–4325 (1980)) is preferably used.

Following the DNA extraction, the RFLP analysis is performed for each individual in the hybrid population using a DNA marker, i.e., a DNA fragment which is capable of detecting polymorphism between the parents of the hybrid population. For rice, DNA markers are available from the Genome Research Team (National Institute of Agrobiological Resources, the Japanese Ministry of Agriculture, Forestry and Fisheries), for use in the RFLP analysis. Typically, an analysis is first conducted by using land markers. Then, the land marker which has exhibited polymorphism is selected and a marker which is located in the vicinity thereof is used for a further analysis to deduce the position of the target gene. The RFLP analysis is well known to those skilled in the art. See, for example, Special Issue of Cell Technology, Plant Cell Technology Series 2, "PCR experimental protocol for plants" (edited by Shimamoto I. and Sasaki T., published by Shujun sha, Apr. 10, 1995).

Briefly, genomic DNAs extracted from individuals are respectively digested with a panel containing a combination of suitable restriction enzymes, thereby obtaining restriction fragments. Then, the restriction fragments are separated from one another by electrophoresis using an agarose gel, or the like. The samples containing respective restriction fragments are generally loaded in adjacent lanes on the gel so as to facilitate the subsequent comparison. After the electrophoresis, a southern hybridization is performed using, as a probe, a DNA marker which has been detectably labelled with a radioactive label (e.g., a radioisotope label) or a nonradioactive label (e.g., biotin or peroxidase label) according to a method which is routinely employed in the art. Then, the bands obtained by the hybridization are visualized by any suitable method (e.g., exposure of the label signals to an X-ray film) and compared with each other so as to detect the polymorphism.

Then, for each individual, the genotype for each marker is analyzed. Based on the obtained data, the linkage may be detected and a genetic distance may be calculated for each of the possible combinations of two gene loci, after which the entire gene loci genes may be aligned so as to create the linkage map. Sequences of gene loci are repeatedly determined based on a three-point test.

The method for calculating the recombination value and the method for converting the recombination value to a genetic distance are well known in the art. See, for example, Allard, R. W., HILGARDIA 24, 235–278 (1956) and Kosambi., Ann. Engenics 12:505–525 (1944). More conveniently, the analytic software "MAPMAKER" (provided by Whitehead Institute for Biomedical Research/MIT Center for Genome Research) can be used for calculating a recombination value, converting the recombination value to a genetic distance, and creating a linkage map.

The linkage analysis based on the polymorphism can also identify a DNA marker which is closely linked to a useful gene of the crop (e.g., a gene related to one of various traits such as the disease resistance and the insect resistance). By using the obtained DNA marker to test the presence of the useful gene, efficient breeding can be performed.

The term "a DNA marker which is closely linked to a gene as used herein refers to a DNA marker such that the distance between a gene and the DNA marker is about 0 cM to about 5 cM.

The term "the gene controlling the rice blast resistance" as used herein refers to a gene which expresses a trait of exhibiting a resistance to rice blast, a disease mediated by *Pyricularia oryzae* (i.e., controls the resistance). In the present specification, the term "rice blast resistance gene" is used interchangeably with the term "the gene controlling the rice blast resistance". As described above, the rice blast resistance is further classified, by its resistance mechanism, into: the true resistance which is controlled by a single gene; and the field resistance which is controlled by a plurality of genes.

Varieties from which the gene controlling the rice blast field resistance can be derived are typically Japanese upland rice varieties including Owarihatamochi, Sensho, etc.

(RAPD and other Analyses)

The RAPD analysis is also applicable to the present invention. This technique is based on the difference in the number and the length (i.e., polymorphism) of amplified fragments obtained by using a PCR method. In particular, various DNA fragments may be amplified by using a short DNA chain of about 10 to 20 bases as a primer and performing a PCR reaction with the entire chromosomal DNA of an organism as a template. A mutation in a binding site of the primer among individuals or lines may result in differences among the amplified fragments. These differences are referred to as the arbitrary amplified DNA fragment polymorphism. The differences are compared to determine the genotype. Operations such as the extraction of DNA or the detection of hybridization can be performed as in the RFLP analysis.

The present invention may also be practiced by utilizing various other techniques of polymorphism detection, as described below. Operation conditions for such techniques are known to, and appropriately selected by, those skilled in the art.

Simple sequence repeat (SSR) analysis, also referred to as simple sequence length polymorphism (SSLP) analysis, is based on the fact that within the genomes of higher organisms, hypervariable regions comprised of tandemly repeated DNA sequences are interspersed. A class of such regions is referred to as "microsatellites" or "simple sequence repeats (SSR)", where the basic repeat unit is around 2–8 bases pairs in length. Hybridization to restricted DNA with microsatellite probes gives multilocus patterns which can resolve variation at the levels of populations and individuals, reflecting changes in the number of copies of the basic repeat.

Amplified fragment length polymorphism (AFLP) is a recently developed technique which is improved over the RAPD analysis in terms of reproducibility. The AFLP analysis involves restriction digestion of the genomic DNA, followed by addition of adaptors to the ends of the digested fragments to provide known sequences for PCR amplification. Primers are then designed so that they incorporate the known adaptor sequence plus 1, 2 or 3 additional base pairs. Thus, PCR amplification occurs only where the primers are able to anneal to fragments which have the adaptor sequence plus base pairs complimentary to the additional base pairs.

Cleaved Amplified Polymorphic Sequence (CAPS) analysis is another technique available for polymorphism detection, which is also referred to as PCR-RFLP. In this case, digestion with a specific restriction enzyme is applied to DNA fragments which have previously amplified by PCR.

(Quantitative Trait Loci (QTL) Analysis)

As described above, the field resistance to rice blast is controlled by a plurality of genes. Therefore, there are a plurality of gene loci related to the field resistance. Such a trait which is controlled by a plurality of genes (herein, the resistance) is called a quantitative, trait (QT). The gene loci related to the quantitative trait is called quantitative trait loci (QTL). In order to identify the QTL, a QTL analysis based on a polymorphism analysis (e.g., an RFLP analysis) may be use. See Lander, E. S. and Botstein D., Genetics 121: 185–199 (1989) for a typical analysis method. Also, a QTL analysis software (e.g., MAPMAKER/QTL, provided by Whitehead Institute for Biomedical Research/MIT Center for Genome Research) is available.

In the context of the present invention, in order to identify the gene locus related to the field resistance to rice blast, a variety having field resistance is crossed with another variety lacking field resistance so as to produce a hybrid population. The phrase "having field resistance" to rice blast as used herein means that the resistance of the variety or the individual exhibits a score of about 6 or less, preferably about 4 or less and, more preferably about 2 or less based on the examination standard for the characteristic test for rice leaf blast, as described below, and the phrase "lacking field resistance" as used herein means that the resistance of the variety or the individual exhibits a score of about 7 or more based on the same standard.

Subsequently, a genomic DNA is extracted from each individual of the hybrid population (i.e., the first generation or a progeny thereof) for examining the genotype of DNA markers spanning across the chromosome. The linkage map is created based on the DNA markers. Then, in consideration of the results obtained from the evaluation of field resistance to rice blast by a field test for the resistance, as described below, the individuals of the hybrid population are grouped based on the genotype data obtained for each DNA marker, to see whether differences in the average value among the groups are different.

A deduced QTL exists in the vicinity of the DNA marker for which the most significant difference for the field resistance of each group was found based on the LOD values within a particular chromosomal location in the linkage map. The present inventors have detected a plurality of QTLs related to the field resistance to rice blast. The present inventors have further specified QTLs with a high variation for the resistance phenotype. A QTL with a higher variation for the resistance phenotype has a greater contribution to the mutation in the degree of susceptibility of the entire line.

(Field Test for Rice Blast Resistance)

The term "field test for the rice blast resistance" as used herein refers to a test in which a rice plant is infected with rice blast in the field so as to determine the rice blast resistance of the rice based on the degree of susceptibility or resistance. An exemplary field test for rice blast includes the nursery test. When a rice nursery is seeded with rice grains in autumn while using a large amount of nitrogen, the rice will suffer from a dramatic degree of rice leaf blast during its seedling stage. The "nursery test" is a test conducted under such a condition. The test is commonly used in the art for testing the rice blast resistance of a variety or a line (see, for example, Agricultural Research Center Research Report No. 30 (1995)).

(Specifying DNA Marker which is Closely Linked to Gene Controlling Rice Blast Field Resistance)

Once a QTL is specified, it may be tested whether the QTL is actually related to the trait of the rice blast resistance. In the genetic background of a lowland rice variety lacking field resistance, an individual having only one of the plurality of QTLs can be selected by using a polymorphism analysis with the above-described DNA marker. By performing the field test for the rice blast resistance and the polymorphism analysis with the DNA marker as described above in the self-propagation progeny line of the individual, it is possible to determine whether the QTL is related to the trait of the rice blast resistance. As a QTL which plays an important role for expressing the rice blast resistance, the present inventors have specified a chromosomal location of the gene controlling the field resistance to rice blast which is derived from Owarihatamochi, and named the gene as pi21(t).

When the gene controlling the field resistance to rice blast is specified as described above, the DNA marker which is closely linked to the gene can also be specified as a marker useful in detecting the presence of the gene. The method for identifying the field resistance to rice blast according to the present invention can be carried out by using the specified useful marker. Moreover, a novel rice variety having field resistance to rice blast can be bred based on this identification method.

The present invention will now be described in greater detail by way of illustrative examples. The restriction enzymes, reagents, etc., which are used in any of the following examples and whose sources are not specified therein, are all available from Takara Shuzo K. K. and/or Toyobo K. K.

EXAMPLE 1

Specifying Chromosomal Location Related to Rice Blast Field Resistance Derived from Owarihatamochi More than 40% of the DNA markers in the rice linkage map exhibit polymorphism between a lowland rice variety and a upland rice variety. Based on this, the present inventors studied the chromosomal locations related to the trait of the field resistance to rice blast in a Japanese upland rice variety.

A QTL analysis was conducted for the F4 generation of a line which was obtained by crossing Owarihatamochi, a Japanese upland rice variety having a high degree of field resistance, with Nipponbare, a Japanese lowland rice variety having a low degree of field resistance. The two varieties were crossed according to a hot water emasculation method ("Rice Breeding Manual", Agricultural Research Center Research Report No. 30, pp. 176–180 (1995)).

Seed for rice variety Owarihatamochi were deposited on Jan. 29, 2004 with accession designation FERM BP-08604 under the Budapest Treaty with the International Patent Organism Depository, National Institute of Advanced Industrial Science and Technology located at AIST Tsukuba Central 6, 1-1, Higashi 1-Chome Tsukuba-shi, Ibaraki-ken 305-8566 Japan.

(1.1 RFLP Analysis)

(a) Extraction of Rice Genomic DNA

The rice genomic DNA was collected by a CTAB method (see Murray M. G. and Thompson W. F., supra) from seedlings of 145 individuals of the F4 generation (b) RFLP Analysis The genomic DNA samples for the 145 individuals extracted in (1) above were processed with a panel of the following restriction enzymes: Apa I, Bam HI, Kpn I, Bgl II, Dra I, Eco RI, Hind III, and Eco RV. After an electrophoresis on a 0.8% agarose gel, a capillary blotting by an alkali method (Sambrook, et al., Molecular Cloning, 2nd edition, 1989) was performed, thereby transferring the respective restriction fragments to a positively charged nylon film (Beoringer). The nylon film was washed at 2×ssc, dried, and treated at 120° C. for 20 mins, thereby immobilizing the DNA on the film. An ECL nucleic acid labeling/detection system (Amersham) was used for hybridization with 62 DNA markers (Table 1) provided by the Genome Research Program (RGP) (Society for Techno-innovation of Agriculture, Forestry and Fisheries (STAFF)) as probes. Then, the label signals were detected to determine the bandpattern of the DNAs. Based on the results, the genotype of each individual of the F4 generation was determined so as to create the linkage map.

TABLE 1

|  | Chromosome | RFLP markers |
|---|---|---|
| 1. | 1 | C112 |
| 2. | 1 | G2200 |
| 3. | 1 | XNpb147 |
| 4. | 1 | XNpb201 |
| 5. | 1 | Y2746L |
| 6. | 1 | R210 |
| 7. | 1 | C131 |
| 8. | 2 | Y8007R |
| 9. | 2 | C601 |
| 10. | 2 | C920 |
| 11. | 2 | C777 |
| 12. | 2 | C149 |
| 13. | 2 | R459 |
| 14. | 3 | G1318 |
| 15. | 3 | C746 |
| 16. | 3 | XNpb15 |
| 17. | 3 | C53 |
| 18. | 3 | C74 |
| 19. | 4 | G177 |
| 20. | 4 | Y8026L |
| 21. | 4 | R738 |
| 22. | 4 | C513 |
| 23. | 4 | G271 |
| 24. | 4 | G317 |
| 25. | 4 | XNpb237 |
| 26. | 4 | XNpb203 |
| 27. | 5 | XNpb109 |
| 28. | 5 | G81 |
| 29. | 5 | XNpb297 |
| 30. | 6 | C952 |
| 31. | 6 | C764 |
| 32. | 6 | C226A |
| 33. | 6 | R1679 |
| 34. | 6 | G122 |
| 35. | 6 | G342 |
| 36. | 7 | C1023B |
| 37. | 7 | R2401 |

TABLE 1-continued

|  | Chromosome | RFLP markers |
|---|---|---|
| 38. | 7 | C1237 |
| 39. | 7 | C507 |
| 40. | 8 | XNpb397 |
| 41. | 8 | G56 |
| 42. | 8 | XNpb369 |
| 43. | 8 | XNpb41 |
| 44. | 9 | rDNA |
| 45. | 9 | G103 |
| 46. | 9 | XNpb13 |
| 47. | 9 | XNpb293 |
| 48. | 10 | L169 |
| 49. | 10 | G1125 |
| 50. | 10 | XNpb133 |
| 51. | 11 | L190 |
| 52. | 11 | G1465 |
| 53. | 11 | C6 |
| 54. | 11 | G257 |
| 55. | 11 | G202 |
| 56. | 11 | G320 |
| 57. | 11 | G189 |
| 58. | 12 | G1106 |
| 59. | 12 | G402 |
| 60. | 12 | G2140 |
| 61. | 12 | XNpb336 |
| 62. | 12 | G1112 |

(1.2 Field Test for Rice Blast Resistance)

(a) Seeding Method

A field was partitioned by appropriately providing seeding grooves, and provided with a basal fertilizer in the amount of about 2 kg/are (a) based on the N (nitrogen) component. Seeds from the above-described F4 generation were seeded on the field and covered with a soil. Then, a herbicide was sprinkled across the field. An additional fertilizer was provided 2–3 times for every 7–10 days each in the amount of about 0.5 kg/a based on the N component.

(b) Examination on Susceptibility Degree

At the time of the above seeding, seeds of other control varieties (Table 2) were seeded at several locations in the field along with the tested individuals in order to generally grasp the state of infected individuals in the field. Diseased leaves by *Pyricularia oryzae* were sprayed on seedlings of rice varieties tested. Based on the examination standard for the characteristic test (Table 3), the degree of susceptibility for each of the tested individuals was determined with 11 (0–10) grades. The examination was performed three times in total, i.e., at the initial, intermediate and late stages of pathopoiesis.

TABLE 2

Differential Varieties for Identifying Race of Rice Blast Fungus

| Differential variety | Resistance gene | Code No. |
|---|---|---|
| Shin No. 2 | Pi-k$^5$ (+) | 1 |
| Aichi Asahi. | Pi-a | 2 |
| Ishikari Shirage | Pi-i | 4 |
| Kanto No. 51 | Pi-k | 10 |
| Tsuyuake | Pi-k" | 20 |
| Fukunishiki | Pi-z | 40 |
| Yashiromochi | Pi-ta | 100 |
| Pi No. 4 | Pi-ta$^3$ | 200 |
| Toride No. 1 | Pi-x$^1$ | 400 |
| BL1 | Pi-b |  |
| K59 | Pi-t |  |

TABLE 3

Evaluation Standard for Resistance to Rice Blast

| Degree of pathopoiesis | Description of pathopoiesis | Area (%) of specks |
|---|---|---|
| 0 | No S-type speck observed 0% | 0% |
| 1 | Little S-type speck observed | 1 |
| 2 | Apparent S-type speck observed | 2 |
| 3 | Moderate S-type speck observed | 5 |
| 4 | High S-type speck observed | 10 |
| 5 | Considerable S-type speck or little leaf death observed | 20 |
| 6 | Apparent leaf death observed | 40 |
| 7 | Moderate leaf death observed | 60 |
| 8 | High leaf death observed | 80 |
| 9 | Stalk mostly dead | 90 |
| 10 | Stalk completely dead | 100 |

(c) Evaluation of Field Resistance

At the time of the above seeding, seeds of field resistance reference varieties of different genotypes (Table 4) were seeded at several locations in the field along with the tested individuals. The field resistance was evaluated by a comparison, in the degree of susceptibility between the reference variety and the tested individuals of the same genotype.

TABLE 4

Field Resistance Reference Varieties

| Degree of resistance | + | Pi-a | PPi-i | PPi-k |
|---|---|---|---|---|
| Strong | Kogane Nishiki Sasaminori | Yamabiko Toyonishiki | Todorokiwase | Tatsumimochi Himenomochi |
| Relatively Strong | Chokai | Kiyonishiki | Yoneshiro | Sakakimochi |
| Moderate | Nipponbare Dewaminori | Kinnanpu Norin No.41 | Fujisaka No. 5 | Mangetsumo-chi Ugonishiki |
| Relatively weak | Sekiminori | Sasanishiki | Asaake | Dewanomochi |
| Weak | Norin No. 29 | Aichi Asahi | Inabawase | Kusabue |

(1.3 Quantitative Trait Locus (QTL) Analysis)

A quantitative trait locus (QTL) analysis was performed for the results of the RPLP analysis described in 1.1 above and the results of the field test described in 1.2 above using the analysis software, MAPMAKER/QTL (supra). It was assumed that a QTL exists in a chromosomal location where the LCD value (threshold) is about 2.0 or more. Five QTLs related to the field resistance to rice blast were detected on chromosomes 2, 4, 9 and 12 (see Table 5).

TABLE 5

Markers linked to QTLs conferring field resistance to rice blast

| Markers linked | Chormosomes | Origin of resistance[1] | LOD[2] | % variation explained[2] |
|---|---|---|---|---|
| G271 | 4 | O | 20.5 | 47.8 |
| Y8026L | 4 | O | 11.7 | 31.0 |
| G2140 | 12 | O | 4.5 | 13.3 |
| G777 | 2 | O | 2.0 | 6.3 |
| G103 | 9 | N | 2.0 | 6.2 |

[1]O and N indicate Owarihatamochi and Nipponbare, respectively.
[2]LOD and % variation explained were calculated at the putative QTLs by MAPMAKER/OTL(Lander and-Sotstein 1989).

Figure 1:
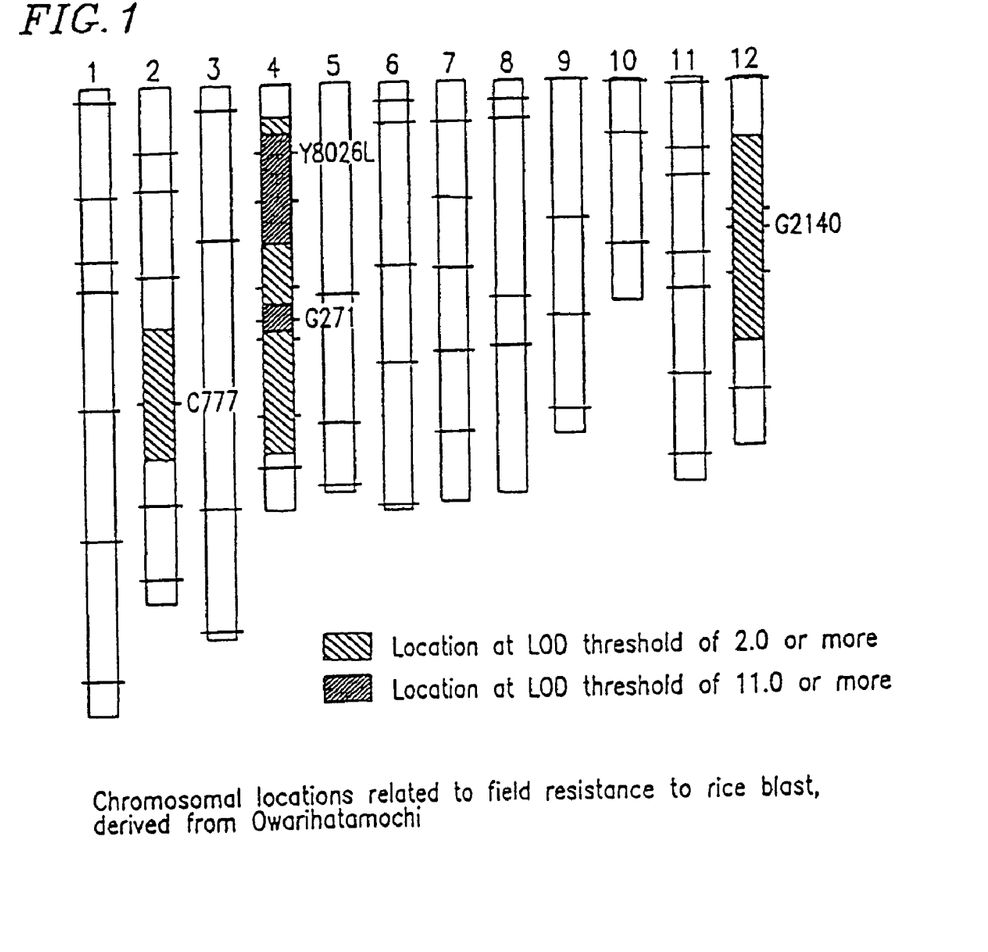
FIG. 1 shows chromosomal locations related to field resistance to rice blast derived from Owarihatamochi in a hybrid population between Owarihatamochi, a Japanese upland rice variety having a field resistance, and Nipponbare, a moderately susceptible Japanese lowland rice variety. A plurality of QTLs (Quantitative Trait Loci) related to the field resistance were detected by a QTL analysis based on the evaluation of the field resistance obtained through a field test and the results of an RFLP analysis using DNA markers. The hatched regions represent locations where the LOD (log-likelihood) value, which is a threshold, was 2.0 or more. The black regions represent locations where the LOD value was 11.0 or more. It was assumed that QTLs exist in chromosomal locations where the LOD value was 2.0 or more. Names of the DNA markers which are linked to the QTLs are also shown in the figure. In the QTL analysis, an analytical software "MAPMAKER/QTL" was used.

Four QTLs located on chromosomes 2, 4 and 12 were from Owarihatamochi, and one QTL located on chromosome 9 was from Nipponbare. Two of the five QTLs were located on chromosome 4. FIG. 1 shows chromosomal locations which are related to the field resistance to rice blast from Owarihatamochi.

The QTL which was linked to the DNA marker G271 was located in the middle of chromosome 4, and exhibited about 47.8% of the phenotypic variance for resistance to rice blast (see Table 5). This value represents the contribution rate of each QTL to the mutation in the degree of susceptibility of the entire line. The other QTL on chromosome 4 exhibited about 31.0% of the phenotypic variance for resistance to rice blast (see Table 5). The results lead to a conclusion that these 2 gene loci on chromosome 4 played a major role in the expression of field resistance in the Japanese upland rice.

Figure 2:
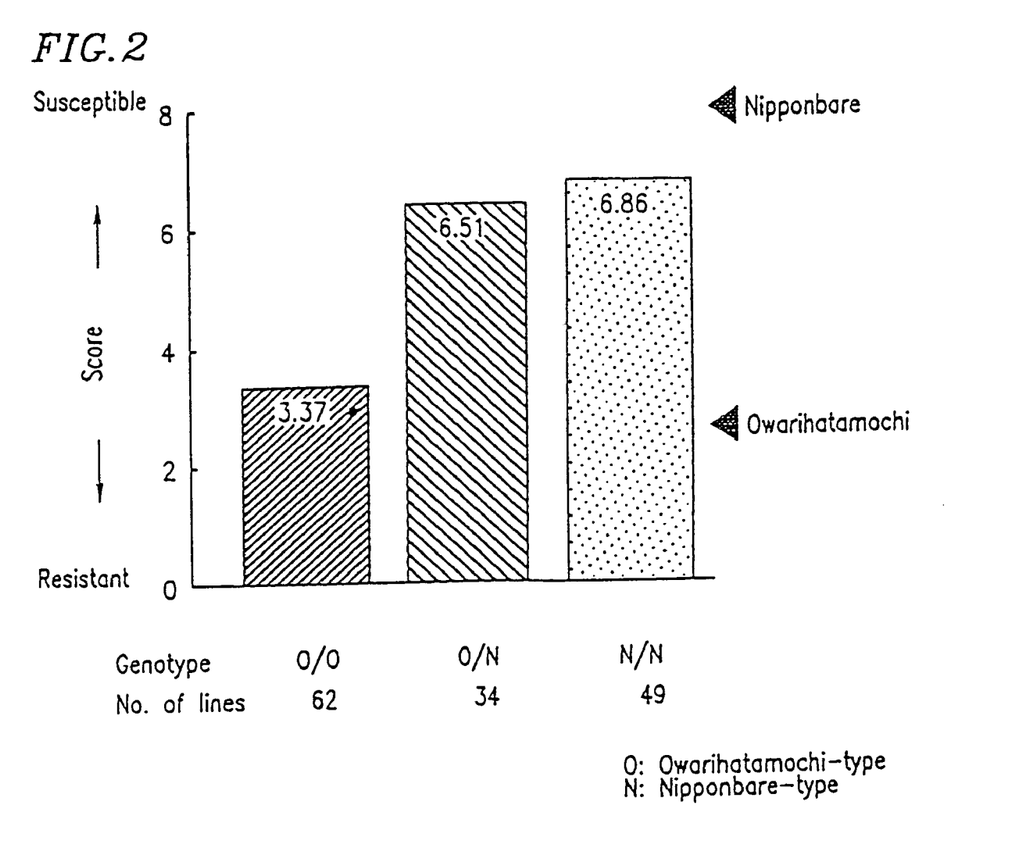
FIG. 2 shows the degree of field resistance in hybrid progeny lines between Nipponbare (N) and Owarihatamochi (O). The degrees of resistance are shown for the respective genotypes (O/O, O/N and N/N) for DNA marker G271. The number of lines tested for each genotype is shown under the genotype name. The degree of resistance is represented as an average score of each group of the lines. The degrees of resistance for Owarihatamochi and Nipponbare are indicated by triangles on the right side of the graph.

The tested 145 individuals were classified according to the genotypes (O/O, O/N and N/N) for G217. The degree of the field resistance to rice blast for each genotype was evaluated based on the results of the field test described in 1.2 above. The results are shown in FIG. 2. The results further support that the QTL which was linked to G217 on chromosome 4 played a major role in the expression of field resistance in the Japanese upland rice.

EXAMPLE 2

Specifying DNA Marker which is closely linked to Gene Controlling Rice Blast Field Resistance The following experiment was conducted to confirm that the QTL which exhibited about 47.8% of phenotypic variation as specified in Example 1 is actually related to the trait of the field resistance to rice blast. A back-crossed plant (96BC131) having only one of the QTLs was generated by crossing Owarihatamochi with Aichi Asahi', a variety which has a low degree of resistance to rice blast, and selecting by an ordinary method with the DNA marker G271. Then, 96BC 131 was used to examine the genotypes of the DNA markers (C777, Y8026L, G271 and G2140) which are linked to the QTLs related to the rice blast field resistance derived from Owarihatamochi, as confirmed in Example 1. As a result, it was found that only the QTL which exhibited about 47.8% of phenotypic variation was included in 968C131 (see Table 6). That is, only the DNA marker (G271) which was linked to this QTL exhibited the genotype of Owarihatamochi, whereas the DNA markers (C777, Y8026L and G2140) which were linked to the other three QTLs did not exhibit the genotype of Owarihatamochi.

TABLE 6

Genotype of DNA marker linked to QTL related to field resistance

| | C777 | Y8026L | G271 | G2140 |
|---|---|---|---|---|
| 96BC131 | — | — | +* | — |
| Owarihataznochi | + | + | + | + |
| Nipponbare | — | — | — | — |
| Aichi Asahi | — | — | — | — |

*"+" indicates having an allele derived from Owarihatamochi

Figure 3:
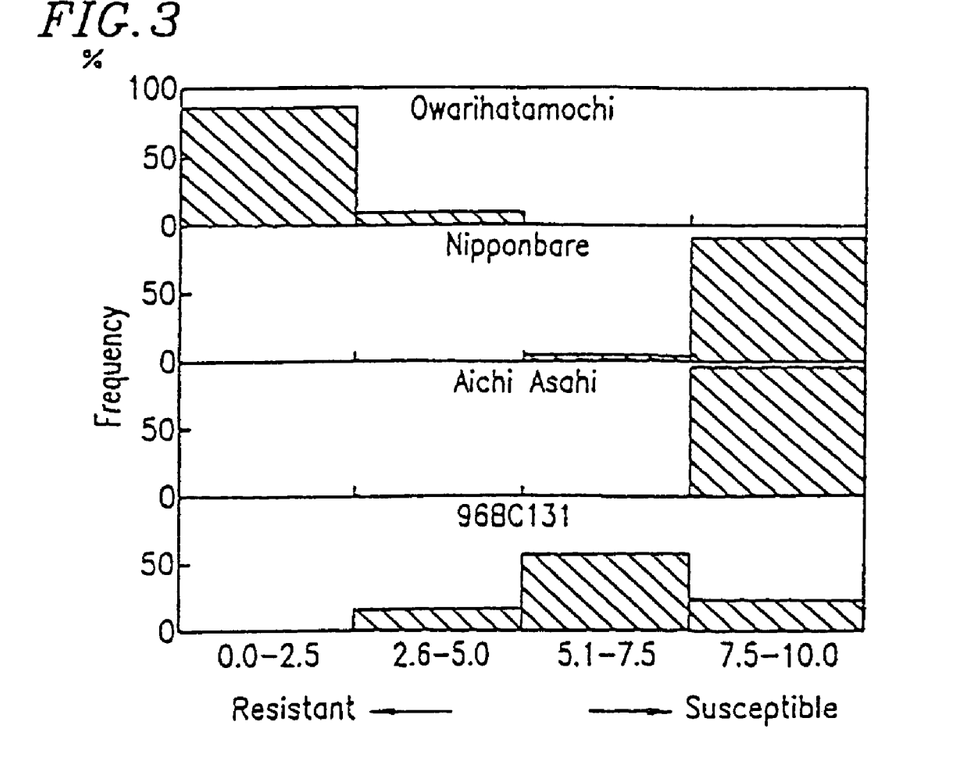
FIG. 3 shows, by the degree of resistance, separation of resistant individuals in a self-propagation progeny population of a backcrossed plant (96BC 131) which was selected using the DNA marker G271. For comparison, the degrees of resistance of Owarihatamochi and Nipponbare, as well as Aichi Asahi which lacks a field resistance, are also shown in the figure.

Then, a field test for rice blast resistance was performed as described in Example 1 in order to test, by the degree of resistance, the separation of the resistance individuals in the self-propagation progeny population of 96BC 131. For comparison, the degree of resistance was tested also for Owarihatamochi (resistant), Nipponbare (moderately susceptible) and Aichi Asahi (susceptible). The results are shown in FIG. 3. It was confirmed that the QTL which exhibited about 47.8% of phenotypic variance was related to the trait of the field resistance to rice blast. The gene in this QTL, which controls the field resistance to rice blast, was named pi21(t).

Figure 4:
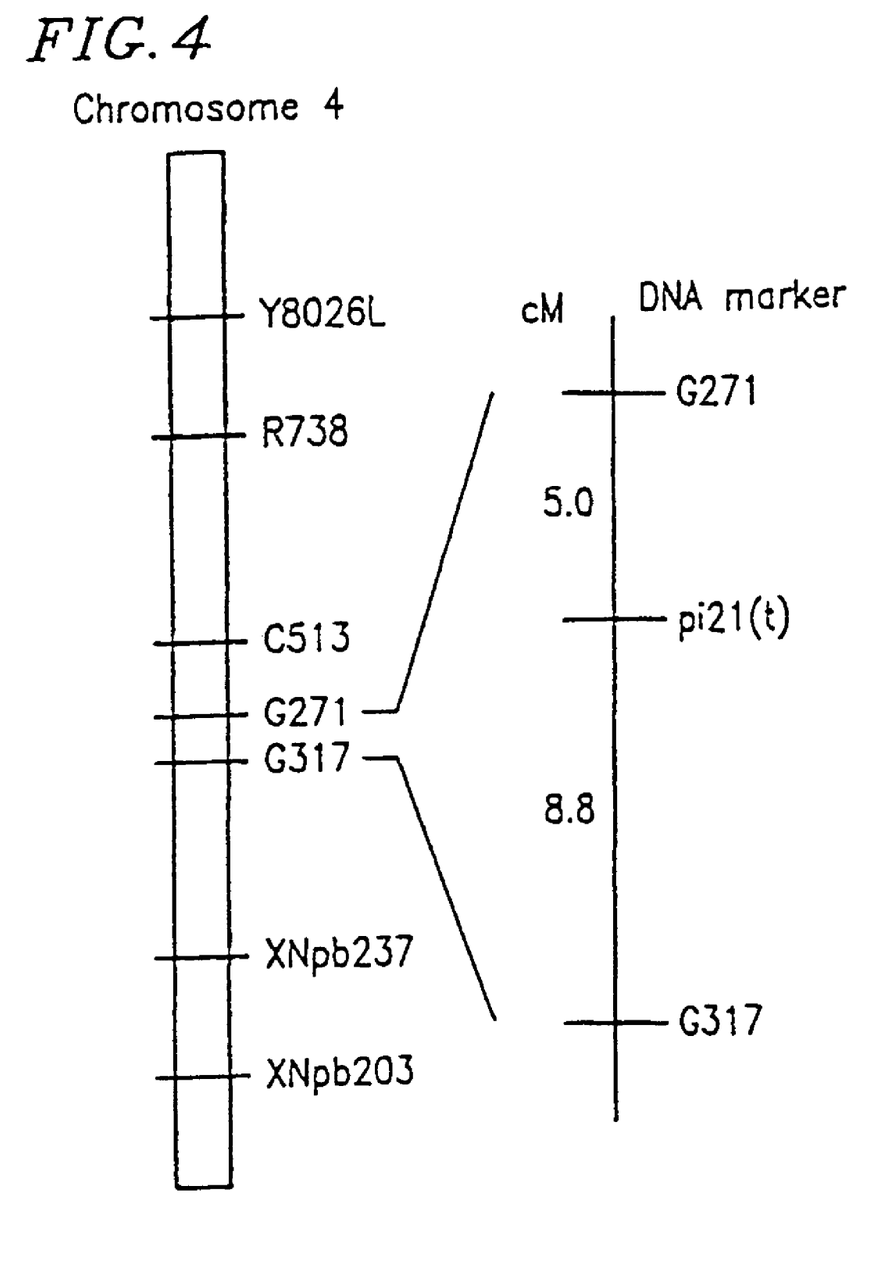
FIG. 4 shows positions on a linkage map for chromosome 4 of the gene pi21(t) controlling the field resistance to rice blast and DNA markers useful in selecting a resistant variety, including G271. In the figure, "cM" represents centimorgan.

FIG. 4 shows the position of the gene pi21(t) controlling the field resistance and the position of the DNA marker G271 in the linkage map created by the trait evaluation results and the polymorphism analysis of Example 1. It is shown that the DNA marker G271 and the gene pi21(t) are linked to each other at 5 cM.

The DNA marker G271 specified by the present inventors is closely linked to the field resistance gene pi21(t-). Therefore, it has been shown that it is possible to indirectly test the field resistance of a rice plant to rice blast by performing a polymorphism analysis using the DNA marker G271.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method for identifying field resistance of a rice plant to rice blast, the method comprising the steps of:
    extracting genomic DNA from the rice plant; and
    detecting the presence or absence of the Owarihatamochi allele of the DNA marker G271 in the genomic DNA by RFLP or CAPS analysis; and
    determining the presence or absence of field resistance based on the presence or absence of the Owarihatamochi allele of the DNA marker G271 in the genomic DNA.

2. A method for breeding a rice variety having field resistance to rice blast, the method comprising the steps of:
    crossing a first rice variety having field resistance to rice blast with a second rice variety lacking the field resistance to rice blast so as to obtain first generation rice varieties;
    extracting genomic DNA from each of the first generation rice varieties or progeny thereof;
    detecting the presence of the Owarihatamochi allele of the DNA marker G271 in the genomic DNA by RFLP or CAPS analysis, thereby determining the presence or absence of field resistance based on the presence or absence of the Owarihatamochi allele of the DNA marker G271 in the genomic DNA; and
    selecting an individual having field resistance.

3. A method for breeding a rice variety having field resistance to rice blast, the method comprising the steps of:
    crossing a first rice variety having field resistance to rice blast with a second rice variety lacking the field resistance to rice blast so as to obtain first generation rice varieties;
    extracting genomic DNA from each of the first generation rice varieties or progeny thereof;
    detecting the presence of the Owarihatamochi allele of the DNA marker G271 in the genomic DNA by RFLP or CAPS analysis;
    determining the presence or absence of field resistance based on the presence or absence of the Owarihatamochi allele of the DNA marker G271 in the genomic DNA; and
    selecting an individual in which field resistance is shown to be present from the first generation rice varieties or the progeny thereof.

* * * * *